(12) United States Patent
Ju et al.

(10) Patent No.: US 9,992,998 B2
(45) Date of Patent: Jun. 12, 2018

(54) RHAMNOLIPID BASED BIOPESTICIDES

(71) Applicants: Lu-Kwang Ju, Akron, OH (US); Ashwin Sancheti, Akron, OH (US)

(72) Inventors: Lu-Kwang Ju, Akron, OH (US); Ashwin Sancheti, Akron, OH (US)

(73) Assignee: The University of Akron, Akron, OH (US)

( * ) Notice: Subject to any disclaimer, the term of this patent is extended or adjusted under 35 U.S.C. 154(b) by 0 days. days.

(21) Appl. No.: 15/463,173

(22) Filed: Mar. 20, 2017

(65) Prior Publication Data

US 2017/0265468 A1    Sep. 21, 2017

Related U.S. Application Data (60) Provisional application No. 62/309,996, filed on Mar. 18, 2016.

(51) Int. Cl.
*A01N 43/16*    (2006.01)

(52) U.S. Cl.
CPC .................................. *A01N 43/16* (2013.01)

(58) Field of Classification Search
CPC ....................................................... A01N 43/16
USPC ....................................................... 504/100
See application file for complete search history.

(56) References Cited

U.S. PATENT DOCUMENTS

| | | | |
|---|---|---|---|
| 5,767,090 A | 6/1998 | Stranghellini et al. | |
| 7,968,499 B2 | 6/2011 | Gandhi et al. | |
| 9,468,700 B2 | 10/2016 | Ju et al. | |
| 2007/0207930 A1* | 9/2007 | Gandhi | A01N 25/30 504/358 |
| 2008/0293570 A1* | 11/2008 | McLaughlin | A01N 25/30 504/101 |
| 2010/0029477 A1* | 2/2010 | McLaughlin | C05D 9/02 504/100 |
| 2011/0319341 A1* | 12/2011 | Awada | A01N 25/30 514/20.9 |
| 2012/0220464 A1 | 8/2012 | Giessler-Blank et al. | |
| 2012/0252066 A1* | 10/2012 | Heng | C12P 19/44 435/69.1 |
| 2014/0106964 A1* | 4/2014 | Jogikalmath | A01C 1/06 504/100 |

* cited by examiner

*Primary Examiner* — Johann R Richter
*Assistant Examiner* — Danielle Sullivan
(74) *Attorney, Agent, or Firm* — Renner, Kenner, Greive, Bobak, Taylor & Weber Co. LPA (57) ABSTRACT

A biopesticide composition includes a solvent and a plurality of rhamnolipid complexes, each rhamnolipid complex including a rhamnolipid complexed with a cation. The biopesticide composition may include a slower-releasing rhamnolipid-based material and a faster-releasing rhamnolipid-based material. The biopesticide composition may be in the form of a coating or a pellet.

9 Claims, 2 Drawing Sheets

RHAMNOLIPID BASED BIOPESTICIDES

CROSS-REFERENCE TO RELATED APPLICATIONS

The present application claims priority to U.S. Provisional Patent Application No. 62/309,996, filed Mar. 18, 2016, incorporated herein by reference.

FIELD OF THE INVENTION

The present invention further relates to rhamnolipid-based biopesticides. The present invention further relates to biopesticides including a slower-releasing rhamnolipid-based material and a faster-releasing rhamnolipid-based material. The present invention further relates to biopesticides including an inner coating layer and an outer coating layer.

BACKGROUND OF THE INVENTION

Rhamnolipids have been found to have antimicrobial properties. They can inhibit microbial growth and damage or kill microbial cells at concentrations above certain critical levels. Because of this antimicrobial activity, rhamnolipids have been reported for potential use as a biopesticide.

Rhamnolipids also have surfactant properties. Based on the surfactant properties, rhamnolipid solutions first act to detach and remove particles (including living organisms, spores, "eggs" of pests) from surfaces of plants. However, microorganisms typically have cell walls to protect them from various harmful factors, including biosurfactants, they may experience in their living environments. While rhamnolipids are effective against many of these walled microbial cells, the concentrations required can be high and the effects may be more of the inhibitory nature, rather than a lethal impact. The use of rhamnolipids at these high concentrations not only makes it costly, but also less selective towards the target pests. That is, at these higher concentrations, rhamnolipids can be inhibitory to multitudes of unintended organisms and actually become ecological stressors to the applied area.

Rhamnolipids also are biodegradable. While this property makes them more environmentally friendly for agricultural uses, it also forces frequent applications to the plants. Requiring frequent applications significantly increases the material, operating, and labor costs for use of rhamnolipids as biopesticides.

It is also taught in the art to prepare calcium rhamnolipid complexes. For example, U.S. Pat. No. 9,468,700 discloses the use of calcium rhamnolipid complexes that are designed to be effective when provided in a wound dressing.

SUMMARY OF THE INVENTION

In a first embodiment, the present invention provides a biopesticide composition comprising a solvent and a plurality of rhamnolipid complexes, each rhamnolipid complex including a rhamnolipid complexed with a cation.

In a second embodiment, the present invention provides a biopesticide composition as in any of the above embodiments, wherein the cation is a metal ion selected from the group consisting of calcium, magnesium, sodium, potassium, manganese, copper, iron, zinc, and aluminum.

In a third embodiment, the present invention provides a biopesticide composition as in any of the above embodiments, wherein the cation is a non-metal ion selected from the group consisting of ammonium, polyamines, polyimines, and chitosan.

In a fourth embodiment, the present invention provides a biopesticide composition as in any of the above embodiments, wherein the solvent is selected from the group consisting of water, ethanol, acetone, and ethyl acetate.

In a fifth embodiment, the present invention provides a biopesticide composition as in any of the above embodiments, wherein the composition further includes an additive selected from the group consisting of dimethicone, soybean oil, ethanol, polyvinyl acetate, gelatin, agar, polyethylene glycol, mineral oil, wax, and combinations thereof.

In a sixth embodiment, the present invention provides a biopesticide composition as in any of the above embodiments, wherein the composition further includes an filler selected from the group consisting of soy flour, talc, carbon powder, graphite powder, celite, zeolite, sand, saw dust, carbon black, clay, bentonite clay, vermiculite, perlite, diatomaceous earth, calcium carbonate, and combinations thereof.

In a seventh embodiment, the present invention provides a method utilizing the biopesticide composition as in any of the above embodiments, comprising the steps of combining the biopesticide composition with a plurality of seeds, and drying the solvent to produce coated seeds.

In an eighth embodiment, the present invention provides a pellet made from a plurality of rhamnolipid complexes, each rhamnolipid complex including a rhamnolipid complexed with a cation.

In a ninth embodiment, the present invention provides a biopesticide composition as in any of the above embodiments, wherein plurality of rhamnolipid complexes includes a first subset of particles including faster-releasing rhamnolipid-based material and a second subset of particles including slower-releasing rhamnolipid-based material, the faster-releasing rhamnolipid-based material characterized as having a rhamnolipid release rate that is faster than the slower-releasing rhamnolipid-based material.

In a tenth embodiment, the present invention provides a biopesticide composition as in any of the above embodiments, wherein the faster-releasing rhamnolipid-based material includes sodium and the slower-releasing rhamnolipid-based material includes calcium.

In an eleventh embodiment, the present invention provides a method utilizing the biopesticide composition as in any of the above embodiments, comprising the step of placing the pellet in proximity with a seed or plant.

In a twelfth embodiment, the present invention provides a coated article comprising an article selected from a seed and a plant, said article having a rhamnolipid-based coating thereon, said coating including a plurality of rhamnolipid complexes, each rhamnolipid complex including a rhamnolipid complexed with a cation.

In a thirteenth embodiment, the present invention provides a coated article as in any of the above embodiments, wherein the coating includes an inner coating and an outer coating.

In a fourteenth embodiment, the present invention provides a coated article as in any of the above embodiments, wherein the inner coating includes a faster-releasing rhamnolipid-based material and the outer coating includes a slower-releasing rhamnolipid-based material, the faster-releasing rhamnolipid-based material characterized as having a rhamnolipid release rate that is faster than the slower-releasing rhamnolipid-based material.

In a fifteenth embodiment, the present invention provides a coated article as in any of the above embodiments, wherein the inner coating includes a slower-releasing rhamnolipid-based material and the outer coating includes a faster-releasing rhamnolipid-based material, the faster-releasing rhamnolipid-based material characterized as having a rhamnolipid release rate that is faster than the slower-releasing rhamnolipid-based material.

In a sixteenth embodiment, the present invention provides a coated article as in any of the above embodiments, wherein the faster-releasing rhamnolipid-based material includes sodium and the slower-releasing rhamnolipid-based material includes calcium.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Embodiments of the invention are based, at least in part, on the use of a rhamnolipid-based material as biopesticides. The rhamnolipid-based material, which may also be referred to as a rhamnolipid-based composition or a rhamnolipid-based biopesticide, includes rhamnolipid complexes, each rhamnolipid complex including at least one rhamnolipid complexed with at least one cation. As used herein, the term "complexed" is defined as forming a complex. As used herein, the term "complex" is defined as a compound with at least one cation bonded with at least one anion. The rhamnolipid complexes may be provided as part of a coating composition or a pellet composition. A coating composition or pellet composition including rhamnolipid complexes may also include one or more of solvents, additives, fillers, and combinations thereof. While it is generally known in the art to use solutions including pure rhamnolipids as biopesticides, the present invention provides one or more improvements over such use of pure rhamnolipids. For example, embodiments of the present invention provide one or more of the following improvements: controlled release of rhamnolipids for more effective treatment, fewer applications of the biopesticide, less vulnerability to being washed away by water, and more effective treatment of wall-less pests and pathogens.

As indicated above, embodiments of the invention provide rhamnolipid complexes including a cation complexed with an anionic rhamnolipid. Based on the ionic charge of a cation or a rhamnolipid, or based on other factors as generally known to those skilled in the art, a rhamnolipid complex may include a plurality of cations, a plurality of anionic rhamnolipids, a plurality of anionic rhamnolipids and other anions, both a plurality of cations and a plurality of anionic rhamnolipids, or both a plurality of cations and a plurality of anionic rhamnolipids and other anions. It is believed that the cation serves to control the release rate of the rhamnolipid complex, thereby allowing the rhamnolipid to serve as the active agent to treat the pathogens.

In one or more embodiments, a rhamnolipids-based material may be characterized by the molar ratio between the cations and the rhamnolipids. It is believed that the molar ratio between the cations and the rhamnolipids generally corresponds to the valence. For a monovalent cation, the molar ratio between the cations and the rhamnolipids may be 1 or approximate thereto. For a bivalent cation, the molar ratio between the cations and the rhamnolipids may be from 0.5 or more to 1 or less. For a trivalent cation, the molar ratio between the cations and the rhamnolipids may be less than 0.5.

As will be described further below, rhamnolipid complexes may be characterized by their release rate or dispersion rate. This is the rate at which the rhamnolipid complexes will dissipate into the surrounding area from the coated article. For offering immediate protection of a seed or plant, the dispersion rate should be at least 0.1 cm/h (2.4 cm/day). Rhamnolipid complexes that disperse slower than this rate may be characterized as a slower-releasing rhamnolipid-based material. Rhamnolipid complexes that disperse faster than this rate may be characterized as a faster-releasing rhamnolipid-based material. In one or more embodiments, the dispersion rate of a rhamnolipid-based material is from 0.1 cm/h or more to 0.2 cm/h or less. In one or more embodiments, the dispersion rate of a rhamnolipid-based material is from 0.15 cm/h or more to 0.25 cm/h or less. In one or more embodiments, the dispersion rate of a rhamnolipid-based material is from 0.03 cm/h or more to 0.06 cm/h or less. In one or more embodiments, the dispersion rate of a rhamnolipid-based material is 0.02 cm/h or less. The dispersion rate may depend on the permeation constant, adsorption constant, and complete concentration profile as a function of position.

In one or more embodiments, a composition includes a slower-releasing rhamnolipid-based material and a faster-releasing rhamnolipid-based material, where "slower-releasing" may be defined as above or as the slower-releasing rhamnolipid-based material having a slower release rate than the faster-releasing rhamnolipid-based material. In embodiments having a slower-releasing rhamnolipid-based material and a faster-releasing rhamnolipid-based material, the protection from pathogens may be extended for longer periods of time, as the faster-releasing rhamnolipid-based material is able to act initially, and then the slower-releasing rhamnolipid-based material is able to provide treatment beyond the treatment time of the faster-releasing rhamnolipid-based material. In one or more embodiments, a composition may include three different rhamnolipid-based materials, each with a different release rate.

The release rate of a rhamnolipid complex may depend on the solubility in water. Dispersion of rhamnolipid complexes in soil involves dissolution into water immediately surrounding the complexes, partition between water phase and the surface of soil matrix (by adsorption), and diffusive and/or convective transport through the water in soil. The dispersion therefore depends on the characteristics of the soil affecting the adsorption affinity of the soil to rhamnolipid complexes and the transport rate, such as convective water flow and the content and channeling of water in the soil.

In one or more embodiments, a rhamnolipid-based material may be characterized by a release rate that corresponds to a predetermined concentration of rhamnolipids in the soil.

In one or more embodiments, the release rate achieves a concentration of rhamnolipids of greater than 8 mg/L, in other embodiments, greater than 15 mg/L, and in other embodiments, greater than 20 mg/L. In one or more embodiments, the release rate achieves a concentration of rhamnolipids of less than 40 mg/L, in other embodiments, less than 30 mg/L, and in other embodiments, less than 25 mg/L. In one or more embodiments, the release rate achieves a concentration of rhamnolipids greater than the critical concentration of rhamnolipids to effectively kill zoospores, which is believed to be in the range of from 8 to 20 mg/L, but not high enough as to harm the seeds.

In one or more embodiments, a rhamnolipid-based material may be characterized by a particular release rate. In one or more embodiments, the release rate of a faster-releasing rhamnolipid-based material, such as sodium-rhamnolipid complexes, is about 10 cm/day, in other embodiments, about 12 cm/day, and in other embodiments, about 14 cm/day. In one or more embodiments, the release rate of a slower-releasing rhamnolipid-based material, such as magnesium-rhamnolipid complexes, is about 0.5 cm/day, in other embodiments, about 1 cm/day, and in other embodiments, about 1.5 cm/day.

It is envisioned that one skilled in the art will be able to tailor the herein described release rate properties to a desired application for a rhamnolipid-based composition.

Pure rhamnolipids are generally acidic. The pH effect of forming rhamnolipid complexes is that the complexes are neutralized compared with the pure rhamnolipids. Sodium rhamnolipid complexes may be prepared by neutralizing a rhamnolipid solution with sodium hydroxide. Calcium or magnesium rhamnolipid complexes may be prepared by reacting a solution of rhamnolipids with the respective metal chloride at neutral pH. In one or more embodiments, a rhamnolipid-based material may be characterized as having a pH of from 6 to 8, in other embodiments, from 6.5 to 7.5, and in other embodiments, 7 or approximate thereto.

In one or more embodiments, the complexation of a composition including cations and anionic rhamnolipid may be substantially complete. As used here, the term "substantially" may refer to an undetectable remainder of non-complexed rhamnolipids, such as by standard anthrone analysis.

The cations may be any positively charged counter-ion. In one or more embodiments, a cation is a metal ion. Suitable metals for use as a metal ion include calcium, magnesium, sodium, potassium, manganese, copper, iron, zinc, and aluminum. In one or more embodiments, a cation is a non-metal positive ion, such as organic compounds, oligomers and polymers, which have positive charges. Suitable non-metal positive ions include ammonium, polyamines, polyimines, and chitosan. Embodiments of the invention provide a rhamnolipids-based material having different types of the above cations.

In one or more embodiments, the cations may be selected based on the desired application. For example, where rhamnolipid complexes are used with a seed or plant, it may be desirable to utilize cations having fertilizing properties, such as potassium and ammonium.

As discussed herein, cations may be characterized by their release rate. Exemplary faster-releasing cations include sodium, ammonium, and potassium. Exemplary slower-releasing cations include magnesium and calcium. Magnesium rhamnolipid complexes release faster than calcium rhamnolipid complexes.

In one or more embodiments, cations may be characterized by their ionic charge. Determining ionic charge is well known to those skilled in the art; for example, calcium ions have 2+ charge. In one or more embodiments, cations and rhamnolipid complex at molar ratios different from their standard ionic charge. For example, for a calcium complex, it might be expected that it will be formed at a molar ratio of 2 rhamnolipid ions per calcium ion. However, embodiments of the invention provide different ratios from this. This is believed to be due to rhamnolipids forming micelles at concentrations higher than the critical micelle concentration. The cations are believed to be complexing with these rhamnolipid assemblies instead of, or in addition to, individual rhamnolipid molecules.

Rhamnolipids (RLs) are a particular glycolipid produced by microorganisms. Rhamnolipids are commonly produced by the fermentation of *Pseudomonas* species. They act as biosurfactants and have antimicrobial activity against various bacteria and fungi. As such, they can be suitably utilized as biopesticides.

Virtually any rhamnolipids may be employed in accordance with this invention. Rhamnolipids occur in two general categories, mono-rhamnolipids and di-rhamnolipids, where mono-rhamnolipids contain one rhamnose residue (hereinafter referred to as R) and di-rhamnolipids contain a chain of two rhamnose residues (hereinafter referred to as R-R).

In one or more embodiments, the one or more lipids of a rhamnolipid include six or more to fourteen or less carbon atoms. In one or more embodiments, a rhamnolipid comprises two lipids, each being a hydroxyl fatty acid chain having from six to fourteen carbon atoms. In one or more embodiments, a rhamnolipid comprises one lipid, the lipid being a hydroxyl fatty acid chain having from six to fourteen carbon atoms. In one or more embodiments, a rhamnolipid comprises two lipids, each being a hydroxyl fatty acid chain having from eight to twelve carbon atoms. In one or more embodiments, a rhamnolipid comprises one lipid, the lipid being a hydroxyl fatty acid chain having from eight to twelve carbon atoms. In one or more embodiments, a rhamnolipid comprises two lipids, each being a hydroxyl fatty acid chain having ten carbon atoms. In one or more embodiments, a rhamnolipid comprises one lipid, the lipid being a hydroxyl fatty acid chain having ten carbon atoms. In one or more embodiments, a mixture of rhamnolipids comprises one or more of the above described rhamnolipids.

In one or more embodiments, rhamnolipids can have one or two molecules of rhamnose linked to a β-hydroxy fatty acid or one or two molecules of rhamnose linked to a chain of two β-hydroxy fatty acids joined by an ester bond. Two specific examples of rhamnolipids are rhamnosyl-β-hydroxydecanoyl-β-hydroxydecanoate ($R-C_{10}-C_{10}$), a mono-rhamnolipid; and rhamnosyl-rhamnosyl-β-hydroxydecanoyl-β-hydroxydecanoate ($R-R-C_{10}-C_{10}$), a di-rhamnolipid. Several homolog molecules with other fatty-acid chains, differing in chain length and/or the extent of saturation, have been identified as rhamnolipids. The rhamnolipids may generally be referred to as $R-C_n$, $R-R-C_n$, $R-C_n-C_m$, or $R-R-C_n-C_m$ where "n" and "m" indicate the number of carbons in each of the hydroxyl fatty acid chains. One or more of the hydroxyl fatty acid chains may also include one or more double bonds as to thereby become an alkene chain.

One method for obtaining rhamnolipids is by way of a fermentation broth. Fermentation is the process that utilizes microorganisms such as bacteria, yeast, and fungi to produce cell biomass and metabolic products. Fermentation methods are generally known to those skilled in the art. In one or more embodiments, rhamnolipids are produced by the fermentation of *Pseudomonas* species. A preferred *Pseudomonas* species is *Pseudomonas aeruginosa*, which produces a mixture of rhamnolipids having ten carbons as the predominant hydroxyl fatty acid chain length.

One or more aspects of the rhamnolipids may be disclosed in PCT Publication No. WO 2015143169, which is incorporated herein by reference.

The rhamnolipid complexes are made by combining a compound that will form cations in order to form complexes with rhamnolipids. For example, a rhamnolipid solution, such as from a fermentation procedure, can be combined with a cation chloride, such as calcium chloride. The pH may be adjusted to about 7. The cations complex with the anionic rhamnolipids to form rhamnolipid complexes as a precipitate. The rhamnolipid complexes may be collected by centrifugation.

Other methods for making rhamnolipid complexes include first dissolving rhamnolipids in water, and then adjusting the pH to about 7 using a base. The base may be a cation hydroxide, such as sodium hydroxide. Then the cations may be added such as in the form of a cation chloride. This allows the cations and rhamnolipids to form complexes. The rhamnolipid complex mixture may be dried to achieve a dry product. The dry product may be crushed into powders for further use. The rhamnolipid complex mixture may also be used as the wet paste mixture without drying. The rhamnolipid complexes may be collected by centrifugation.

Figure 1:
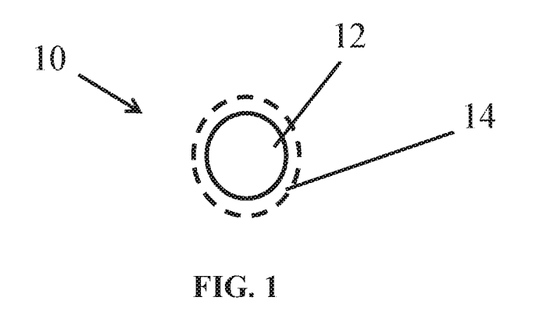
FIG. 1 is a schematic showing a coated article.

With reference to FIG. 1, a coated article, generally indicated by the numeral 10, includes an article 12, such as seed 12 or plant 12, with a rhamnolipid-complex-containing coating 14 thereon. Article 12 may be any suitable seed or plant, such as seeds of plants of soybean, tomato, strawberry, chicory, peppers, alfalfa, avocado, *Pisum sativum* (peas), citrus fruits, potatoes, cocoa, cucumbers, squash, and onions. Article 12 may be a grown seedling, sapling, treelet, or mature plant. In one or more embodiments, seed 12 is 3 mm or greater in size.

In one or more embodiments, rhamnolipid-complex-containing coating 14 includes a slower-releasing rhamnolipid-based material and a faster-releasing rhamnolipid-based material. As described herein, embodiments using a slower-releasing rhamnolipid-based material and a faster-releasing rhamnolipid-based material generally allow the faster-releasing rhamnolipid-based material to provide pathogen treatment for a first time period, and then allow the slower-releasing rhamnolipid-based material to provide pathogen treatment for a second time period beyond the first time period.

Although the coating of FIG. 1 (and FIGS. 2 and 3) is shown as a dashed line, it should be appreciated that these are schematic, sectional representations in order for the underneath article to be visible. Embodiments of the invention provide articles having 100%, or approximate thereto, coverage by a coating. Embodiments of the invention provide articles having 25% or more coverage, in other embodiments, 50% or more coverage, and in other embodiments, 75% or more coverage, by a coating.

Figure 2:
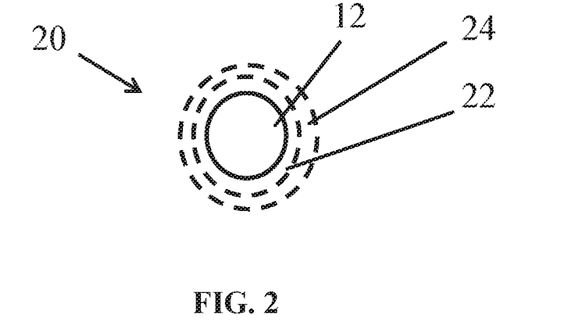
FIG. 2 is a schematic showing an article coated with an inner coating and an outer coating.

With reference to FIG. 2, a coated article, generally indicated by the numeral 20, includes an article 12 with an inner rhamnolipid-complex-containing coating 22 thereon and an outer rhamnolipid-complex-containing coating 24 on inner rhamnolipid-complex-containing coating 22.

In one or more embodiments, inner coating includes a faster-releasing rhamnolipid-based material and outer coating includes a slower-releasing rhamnolipid-based material. With the faster-releasing material in the inner coating, when it separates from a seed coat, it also causes the outer layer of slow-releasing material to fall off the seed coat. These fallen materials will then be near the seed to provide protection. For some seeds, use of a slower-releasing material as the inner coating may tend to restrict the water uptake, seed swelling, or seed coat breakage, and therefore impact germination. Use of the faster-releasing material as the inner coating may offer protection from pests while not affecting seed germination and root growth.

In one or more embodiments, inner coating includes a slower-releasing rhamnolipid-based material and outer coating includes a faster-releasing rhamnolipid-based material. These embodiments may be particularly suitable where the coating is applied on parts of plants that do not restrict normal plant growth, such as stems, branches, barks, and leaves.

The faster-releasing rhamnolipid-based material may provide pathogen treatment for a first time period, and the slower-releasing rhamnolipid-based material may provide pathogen treatment for a second time period beyond the first time period. The desired application will determine whether the faster-releasing rhamnolipid-based material or the slower-releasing rhamnolipid-based material is in the inner coating.

In one or more embodiments, a coating for a coated article may be characterized by the thickness of the coating. In one or more embodiments, a coating thickness is in the range of from 15 micrometers or more to 150 micrometers or less, in other embodiments, from 70 micrometers or more to 110 micrometers or less, and in other embodiments, from 80 micrometers or more to 100 micrometers or less. Where additives for preventing stickiness are utilized, the thickness of a coating may be up to about 500 micrometers.

In one or more embodiments, a coating for a coated article may be characterized by the concentration of the coating. In one or more embodiments, the concentration of rhamnolipid complexes in a coating is 75 wt. % or more, in other embodiments, 80 wt. % or more, in other embodiments, 85 wt. % or more, in other embodiments, 90 wt. % or more, and in other embodiments, 95 wt. % or more. In one or more embodiments, a coating composition includes a concentration of rhamnolipid complexes from 5 to 60 wt. %, in other embodiments, from 20 to 50 wt. %, in other embodiments, from 25 to 40 wt. %, and in other embodiments, from 30 to 35 wt. %. Where additives for preventing stickiness are utilized, the concentration of rhamnolipid complexes in a coating may be from 35 wt. % or more to 60 wt. % or less, in other embodiments, from 40 wt. % or more to 50 wt. % or less, and in other embodiments, 35 wt. % or approximate thereto.

In one or more embodiments, a coating for a coated article may be characterized by an amount of rhamnolipids per seed. In one or more embodiments, a coating composition provides from 10 to 60 mg coating per seed, in other embodiments, from 15 to 50 mg coating per seed, and in other embodiments, from 20 to 30 mg coating per seed. In one or more embodiments, a coating composition provides from 5 to 40 mg of a particular rhamnolipid complex per seed, in other embodiments, from 10 to 35 mg coating per seed, in other embodiments, from 5 to 15 mg coating per seed, and in other embodiments, from 5 to 10 mg coating per seed. In one or more embodiments, a coating composition provides 10 to 35 mg sodium rhamnolipid complexes per seed, in other embodiments, 5 to 15 mg magnesium rhamnolipid complexes, and 5 to 10 mg calcium rhamnolipid complexes.

As stated above, a coating composition including rhamnolipid complexes may also include one or more of solvents, additives, fillers, and combinations thereof. The one or more solvents, additives, fillers are not required, but may be provided based on desirable properties for a coating composition, such as reducing stickiness.

Methods for coating seeds are generally known in the art, with an exemplary method including tumbling the seeds in a hot air dryer along with the coating composition. This deposits a thin layer of coating on the seeds. Where present, the one or more solvents are provided to solubilize the rhamnolipid complexes and other optional additives, in order to provide the rhamnolipid complexes and other optional additives as the coating. The solvent evaporates as part of the coating method. Thus, a desired characteristic of the solvents is fast evaporation in order to reduce contact time during the coating method. Other desired characteristics of the one or more solvents include the ability to dissolve the active ingredients to facilitate the coating, minimal or no toxicity to the seeds and farmers, and minimal or no negative environmental effects.

Solvents may be selected based on the solubility of the rhamnolipid complexes therein. In some embodiments, where the rhamnolipid complexes are not soluble in one solvent, a mixture of more than one solvent can be used. Rhamnolipids are surfactants and therefore can help solubilize solvents that are immiscible. This property also makes the choice and adjustment of solvents more customizable according to the particular application needs. Exemplary solvents include water, ethanol, acetone, and ethyl acetate.

In certain embodiments, it may be desirable to use ethanol as a solvent instead of water in order to reduce the time for coating seeds. This is believed to be based on a reduction in water content, which reduces the drying time.

A coating composition may include one or more additives in order to improve a coating composition or a coating process. The desired characteristics for additives are: reduced cohesion between seeds during the coating process, reduced stickiness after the coating, stability of the coating during storage, and being innocuous to seed germination.

Exemplary additives include dimethicone, soybean oil, ethanol, polyvinyl acetate, gelatin, agar, polyethylene glycol, mineral oil, and wax. Soybean oil may be provided to reduce the cohesive forces in the coating. Ethanol may be provided to decrease the water content and reduce the drying time of the seeds. Dimethicone may be provided to reduce stickiness, particularly where ethanol is utilized as a solvent. Dimethicone may also give a more even coating on the seed surfaces and a more uniform coating from seed to seed.

In certain embodiments, one or more additives may be added during the coating process. In certain embodiments, one or more additives may be premixed with the coating composition prior to the coating process.

A coating composition may be characterized by the concentration of one or more additives. In one or more embodiments, a coating composition includes a concentration of one or more additives from 0.5 to 15% w/w, in other embodiments, from 1 to 10% w/w, and in other embodiments, from 1 to 5% w/w.

Certain additives may also be described as fillers. Filler materials may be added to normalize the seed size distribution and to prevent agglomeration of seeds. Filler materials may also reduce stickiness and prevent the seeds from caking during storage. Exemplary fillers include soy flour, talc, carbon powder, graphite powder, celite, zeolite, sand, saw dust, carbon black, clay, bentonite clay, vermiculite, perlite, diatomaceous earth, and calcium carbonate.

In certain embodiments, one or more fillers may be added during the coating process. It may be desirable to add the one or more fillers after a time of drying the coating composition in order for an effective amount of the filler to be provided in the coating. In certain embodiments, one or more fillers may be premixed with the coating composition prior to the coating process.

Fillers may also be added to account for the hygroscopic nature of certain rhamnolipid-based materials. Certain rhamnolipid-based materials are believed to absorb moisture, such as during storage, due to the hygroscopic nature of the sugar moieties in the rhamnolipids. This may then cause them to become sticky and cause seed dispersion issues. The hygroscopic tendency varies with the cation used. Generally, sodium rhamnolipid complexes are more hygroscopic than magnesium rhamnolipid complexes, which are more hygroscopic than calcium rhamnolipid complexes. Calcium rhamnolipid complexes have minimal hygroscopic tendency. Moisture absorption itself does not necessarily have any negative effect on the effectiveness of the rhamnolipid-based material, but formation of seed clumps may not be desirable for handling. In one or more embodiments, a rhamnolipid-based material including calcium rhamnolipid complexes may be used as the outer layer of coating to prevent seed stickiness. In one or more embodiments, and other less hygroscopic rhamnolipids-mineral complexes, such as those with ferric ions, may be used as the outer layer of coating to prevent seed stickiness. In one or more embodiments, a hydrophobic filler in the coating may be used to prevent or minimize this moisture absorbtion issue.

Since certain additives are provided to reduce stickiness of a coating composition, it may be desirable to avoid or reduce the stickiness problem prior to producing the coating composition. In certain embodiments where the rhamnolipids are made in a fermentation procedure, the resulting fermentation product contains from about 90 to 92% of rhamnolipids. In one or more embodiments, this fermentation product can be water washed with an acidic water in order to remove certain minor components or impurities. The acidic water may have a pH of from about 2.5 to 3.0. Following the water wash, the rhamnolipids product may have a purity of about 95 to 96%.

As said above, methods for coating seeds are generally known in the art. Suitable methods include hot air drying, spray coating, dip coating, rotating drum coating, tumbler coating, and combinations thereof. As an example, the desired rhamnolipid-based coating composition may first be added to a vessel, such as a rotating coating chamber. When the consistency and viscosity of the rhamnolipid-based coating composition is at the desirable point, such as by solvent vaporization, the seeds are added and then coated by the rhamnolipid-based coating composition. If desirable, an additive may later be added to form an outer layer in order to minimize clumping of seeds. The coated seeds may then be stored in dry conditions, with or without desiccation or vacuum packaging.

Figure 3:
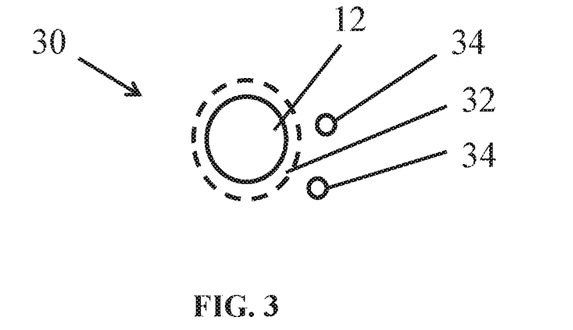
FIG. 3 is a schematic showing a coated article provided in conjunction with separate rhamnolipid-based pellets.

With reference to FIG. 3, a coated article, generally indicated by the numeral 30, includes an article 12 with a rhamnolipid-complex-containing coating 32 thereon. Coated article 30 may be provided with a plurality of pellets 34. Methods of making pellets are generally known in the art. An exemplary method includes first forming a wet rhamnolipid complex composition, and then drying the wet composition in polyethylene terephthalate (PET) molds to produce small pellets including dried rhamnolipid complexes. In one or more embodiments, rhamnolipid-complex-containing coating 32 includes a faster-releasing rhamnolipid-based material and pellets 34 include a slower-releasing rhamnolipid-based material. Thus, as described herein, the faster-releasing rhamnolipid-based material provides pathogen treatment for a first time period, and slower-releasing rhamnolipid-based material provides pathogen treatment for a second time period beyond the first time period.

Figure 4:
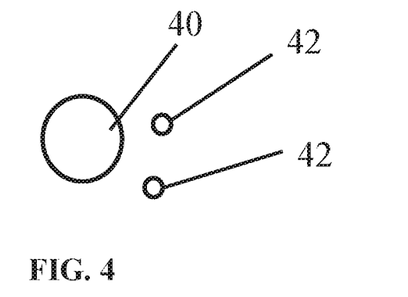
FIG. 4 is a schematic showing an uncoated article provided in conjunction with separate rhamnolipid-based pellets.

With reference to FIG. 4, an uncoated article 40, such as seed 40 or plant 40, may be provided with a plurality of rhamnolipid-complex-containing pellets 42. Article 40 may be any suitable seed or plant, such as seeds of plants of soybean, tomato, strawberry, chicory, peppers, alfalfa, avocado, *Pisum sativum* (peas), citrus fruits, potatoes, cocoa, cucumbers, squash, and onions. Article 40 may be a grown seedling, sapling, treelet, or mature plant. In one or more embodiments, rhamnolipid-complex-containing pellets 42 include a slower-releasing rhamnolipid-based material and a faster-releasing rhamnolipid-based material.

Figure 5:
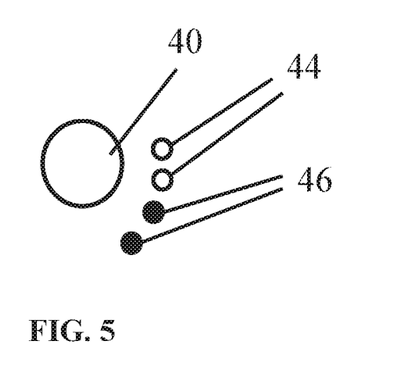
FIG. 5 is a schematic showing an uncoated article provided in conjunction with a first plurality of rhamnolipid-based pellets and a second plurality of rhamnolipid-based pellets.

With reference to FIG. 5, uncoated article 40 may be provided with a first plurality of rhamnolipid-complex-containing pellets 44 and a second plurality of rhamnolipid-complex-containing pellets 46. First plurality of pellets 44 may include a slower-releasing rhamnolipid-based material and second plurality of pellets 46 may include a faster-releasing rhamnolipid-based material A plurality of pellets may be characterized by an average pellet size. In one or more embodiments, a plurality of pellets has an average pellet size of from 0.02 cm or more to 1.5 cm or less, in other embodiments, from 0.05 cm or more to 1 cm or less, and in other embodiments, from 0.1 cm or more to 0.5 cm or less.

In addition to coatings and pellets, rhamnolipid-based materials may be in the form of, or exist as part of, solid powders, fertilizer mixtures, liquid applicator compositions, and spray applicator compositions.

Embodiments of the present invention are desirably used to protect plants and seed against pests or pathogens that do not contain cell walls. The lack of a cell wall may be for the duration of the life cycle, or may be a lack of a cell wall at a disease-related stage in the life cycle. Without cell wall protection, the pests are much more sensitive to rhamnolipids. An exemplary pest is *Phytophthora sojae*, which causes root-rot and other diseases to soy plants. During most of its life cycle, this pest is protected by cell wall and rhamnolipids need to be present in relatively high concentrations to exhibit inhibitory effects on its growth. However, this pest spreads its infection in soil by releasing motile zoospores during wet conditions and the zoospores swim towards roots of soy plants, being attracted by chemicals released by the roots. Once reaching the roots, zoospores attach, germinate, infect, and very often kill the plants. Zoospores are the most commonly implicated life stage responsible for spread of this pest, and many others. In this important stage of asexual reproduction, zoospores are not protected by cell walls. The *P. sojae* zoospores can be almost instantaneously stopped for motility and, shortly after, lysed or killed by rhamnolipids. This is at rhamnolipids concentrations of as low as from 8 to 20 mg/L, as described above.

The *P. sojae* zoospores primarily infect the newly germinated roots from soybean seeds in the first 5-7 days. This is the most critical period that rhamnolipids can be present for controlling the disease. Thus, embodiments of invention provide coatings and pellets that protect the seeds during this time. The rhamnolipid-based material releases rhamnolipids into the water in soil immediately surrounding the seeds. As described above, embodiments provide a release rate to control the releasing of rhamnolipids to be sufficient to match the rate of root growth in this critical 5-7 day period.

The present invention is able to protect various organisms from infectious plant disease. Exemplary organisms include fungi, oomycetes, bacteria, viruses, viroids, virus-like organisms, phytoplasmas, protozoa, nematodes, and parasitic plants. It is believed that phytoplasmas, protozoa, oomycetes, and some fungal divisions such as chytridiomycota and hyphochytridiomycota, may be among the pests most effectively controlled by the rhamnolipid-based materials. Phytoplasmas and protozoa do not have cell wall. Organisms in the divisions of oomycota, chytridiomycota and hyphochytridiomycota have cell walls during most of their life cycles but their zoospores and flagellated gametes (sperms) do not have a cell wall or shed their walls before fusion for sexual reproduction. *P. sojae* belongs to oomycetes.

Some examples of other important diseases caused by these pests, and which are prevented by the rhamnolipid-based materials, are given in the following table. The infectious and/or reproductive mechanisms of these pathogens are generally similar to *P. sojae*. The described rhamnolipid-based materials may be utilized as a wide spectrum biopesticide agent.

TABLE 1

Pathogens treatable by rhamnolipids-based materials

| Group | Species | Plant infected; Disease |
|---|---|---|
| Oomycota | *Phytophthora infestans* | potato and tomato; late blight |
| | *Ph. ramorum* | oak trees, native shrubs, herbaceous plants, and woody ornamental plants; sudden oak death, leaf and shoot blight |
| | *Ph. capsici* | cucurbits (cantaloupe, cucumber, gourd, honeydew, pumpkin, squash, watermelon), eggplant, peppers, tomatoes, and other vegetable and weed species. |
| | *Ph. cinnamomi* | azalea, *rhododendron, camellia*, boxwood, *eucalyptus*, avocado, pine, juniper, hemlock, spruce, fir, cedar & cypress |
| | *Pythium aphanidermatum* | turf grass; infects seeds, juvenile tissue, lower stems, fruit rot and roots |
| | *Py. irregulare* | pineapple, cereals, grasses, celery, pepper, tobacco, pecan trees, citrus trees, strawberries, lentils, corn, soybean, cucumber, onion, carrot & many floricultural crops; damping off & root rot |
| | *Py. myriotylum* | tomato, peanut, tobacco; damping off, root rot, death of seedling and damage to older plants |
| | *Py. ultimum* | cabbage, carrot, cucumber, melon, turf grass, wheat |
| | *Py. graminicola* | pineapples, turf grass, |
| | *Py. helicoides* | miniature roses, herb and other plants; root rot |
| | *Py. dissotocum* | tobacco, lettuce, spinach |
| | *Saprolegnia* and *Achlya* spp. | freshwater saprotrophs (also, parasites of salmonid fish) |
| | *Aphanomyces* spp. | pea, spinach |

TABLE 1-continued

Pathogens treatable by rhamnolipids-based materials

| Group | Species | Plant infected; Disease |
|---|---|---|
| Chytridiomycota | Olipidum brassicae, O. radicale | zoospores are vector of several plant viruses, cabbage |
| | Synchytrium endobioticum | Potato wart disease |
| | Neocallimastix spp. | obligatory anaerobic saprotrophs, cellulose breakdown |
| Plasmodiophorids | Plasmodiophora brassicae | cruciferous species such as cabbage, collards, kale, mustard, Brussel sprouts, radish, turnip, rutabaga, cauliflower, broccoli, rape, and kohlrabi; club root disease |
| | Polymyxa graminis, P. betae | lettuce, barley, wheat, melon, cucumber, rice, peanut, oat, potato, beet |
| | Spongospora subterranea | potato, tomato; powdery scab, vector for potato mop-top virus |

In light of the foregoing, it should be appreciated that the present invention advances the art by providing improved rhamnolipid-based biopesticides. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Comparative 1

Three soybean seeds were coated with pure rhamnolipids (a highly viscous glue-like material) without modifications. Three soybean seeds were uncoated. After a period of six days, the seeds coated with pure rhamnolipids did not germinate and experienced rot and mold growth. The three uncoated seeds germinated normally. It is believed that the pure rhamnolipids did not germinate due to the acidity of the pure rhamnolipids causing localized high acidity.

Comparative 2

The effects of acidity and concentration were measured by contacting soybean seeds with pH-neutralized pure rhamnolipid solutions of different concentrations, ranging from 0 to 90 g/L. The seed germinated normally at a concentration of 5 g/L neutralized pure rhamnolipids. Seeds at 10 g/L and 30 g/L germinated partially, but the growth was stunted and black spots were visible. Seeds did not germinate at pH-neutralized pure rhamnolipid concentrations of 50 g/L and above.

Comparative 3

Uncoated seeds were tested for germination percentage. These uncoated seeds were split into two groups: one group exposed to P. sojae zoospores and one group without exposure to P. sojae zoospores. The soil with planted seeds was inoculated with P. sojae zoospores for the exposed group, and just water for the unexposed group, 1 day after the seed planting. The uncoated seeds without exposure to P. sojae zoospores germinated normally (100%) as expected, while only 20-60% (in different batches of experiments) of the uncoated seeds in soil inoculated with P. sojae zoospores germinated, clearly showing the root-rot disease caused by the P. sojae zoospores.

Example 1

Sodium rhamnolipid complex was prepared by dissolving rhamnolipid in water with the addition of sodium hydroxide to neutralize pH. Then, water was vaporized to obtain the dry complex. Sodium rhamnolipid complex was found to be much more soluble in water and faster to release and disperse in wet soil than was calcium rhamnolipid complex.

The same experiment as Comparative 3 was performed for seeds coated with the sodium rhamnolipid complex. That is, a first group was exposed to P. sojae zoospores and a second group was without exposure to P. sojae zoospores. Both the exposed group and the unexposed group germinated at 100% success rate. The sodium rhamnolipid complex coating successfully protected the seeds from the P. sojae zoospores.

Example 2

Calcium rhamnolipid complex was prepared by first dissolving rhamnolipids in water with pH adjustment to about 7 using sodium hydroxide. Calcium chloride was then added. Calcium complex formed was collected by centrifugation. When calcium chloride was added at an equimolar ratio to rhamnolipids, the remaining rhamnolipid concentration in the solution was about 450 mg/L.

The same experiment as Comparative 3 was performed for seeds coated with the calcium rhamnolipid complex. That is, a first group was exposed to P. sojae zoospores and a second group was without exposure to P. sojae zoospores. Both the exposed group and the unexposed group germinated at 60% success rate. The calcium rhamnolipid complex coating protected the seeds from the P. sojae zoospores compared to the exposed Comparative 3 group. The calcium rhamnolipid complex coating for the unexposed seeds resulted in a lower germination rate than the uncoated, unexposed Comparative 3 group. Since calcium rhamnolipid complexes dissolve slowly in wet soil, if coated in large enough amounts, the calcium rhamnolipid complex might restrict seed germination. This might be due to inhibition of water imbibement and/or prevention of seed coat breakage or embryonic shoot emergence. Thus, as discussed above, certain embodiments of the invention provide a faster-releasing rhamnolipid-based material and a slower-releasing rhamnolipid-based material.

Various modifications and alterations that do not depart from the scope and spirit of this invention will become apparent to those skilled in the art. This invention is not to be duly limited to the illustrative embodiments set forth herein.

What is claimed is:

1. A biopesticide composition consisting of a solvent, a plurality of faster-releasing rhamnolipid complexes characterized by a dispersion rate in soil of at least 0.1 cm/h, and a plurality of slower-releasing rhamnolipid complexes characterized by a dispersion rate in soil of less than 0.1 cm/h, each of the faster-releasing rhamnolipid complexes and slower-releasing rhamnolipid complexes including a rhamnolipid complexed with a cation.

2. The biopesticide composition of claim 1, wherein the cation is a metal ion selected from the group consisting of calcium, magnesium, sodium, potassium, manganese, copper, iron, zinc, and aluminum.

3. The biopesticide composition of claim 1, wherein the cation is a non-metal ion selected from the group consisting of ammonium, polyamines, polyimines, and chitosan.

4. The biopesticide composition of claim 1, wherein the solvent is selected from the group consisting of water, ethanol, acetone, and ethyl acetate.

5. The biopesticide composition of claim 1, wherein the faster-releasing rhamnolipid complexes include sodium rhamnolipid complexes and the slower-releasing rhamnolipid complexes include calcium rhamnolipid complexes.

6. A method of treating a plant or seed with the biopesticide composition of claim 1 comprising
  applying the biopesticide composition to soil, and
  allowing, based on a release rate of the biopesticide composition, the soil to achieve a concentration of rhamnolipids in the range of from 8 to 20 mg/L.

7. The method of claim 6, wherein the step of applying the biopesticide composition includes applying the biopesticide composition in proximity with a seed or plant.

8. A coated article comprising an article selected from a seed and a plant, an inner, faster-releasing, rhamnolipid-based coating on said article, an outer, slower-releasing, rhamnolipid-based coating directly on said inner coating, said inner, faster-releasing, rhamnolipid-based coating including a plurality of faster-releasing rhamnolipid complexes characterized by a rhamnolipid release rate in soil of at least 0.1 cm/h, and said outer, slower-releasing, rhamnolipid-based coating including a plurality of slower-releasing rhamnolipid complexes characterized by a rhamnolipid release rate in soil of less than 0.1 cm/h.

9. The coated article of claim 8, wherein the inner, faster-releasing rhamnolipid-based coating includes sodium and the outer, slower-releasing rhamnolipid-based coating includes calcium.

* * * * *